United States Patent
Pratt et al.

(10) Patent No.: US 6,584,825 B2
(45) Date of Patent: Jul. 1, 2003

(54) METHOD AND APPARATUS FOR DETERMINING THE AMOUNT OF HYDROGEN IN A VESSEL

(75) Inventors: Steven D. Pratt, Plantation, FL (US); Sivakumar Muthuswamy, Plantation, FL (US); Ronald J. Kelley, Coral Springs, FL (US); Robert W. Pennisi, Boca Raton, FL (US)

(73) Assignee: Motorola, Inc., Schaumburg, IL (US)

( * ) Notice: Subject to any disclaimer, the term of this patent is extended or adjusted under 35 U.S.C. 154(b) by 95 days.

(21) Appl. No.: 09/928,607

(22) Filed: Aug. 13, 2001

(65) Prior Publication Data

US 2003/0029224 A1 Feb. 13, 2003

(51) Int. Cl.$^7$ ............................................... G01N 19/10
(52) U.S. Cl. .................... 73/23.2; 73/23.31; 422/88; 702/24
(58) Field of Search ........................ 73/23.2, 23.31, 73/30.02, 31.05; 422/88, 94; 702/24

(56) References Cited

U.S. PATENT DOCUMENTS

| | | | | |
|---|---|---|---|---|
| 4,241,019 A | * | 12/1980 | Nakatani et al. | 422/94 |
| 4,576,640 A | * | 3/1986 | Wootton et al. | 75/123 E |
| 5,635,627 A | * | 6/1997 | Bytyn | 73/31.05 |
| 5,976,725 A | * | 11/1999 | Gamo et al. | 429/25 |
| 6,006,582 A | * | 12/1999 | Bhandari et al. | 73/23.2 |
| 6,450,007 B1 | * | 9/2002 | O'Connor | 73/23.2 |
| 6,474,138 B1 | * | 11/2002 | Chang et al. | 73/25.01 |
| 6,484,563 B1 | * | 11/2002 | Enquist et al. | 73/31.06 |

OTHER PUBLICATIONS

Huston, E.L., Sandrock, G.D., "Engineering Properties of Metal Hydrides," Journal of the Less–Common Metals 74 (1980) 435–443. © Elsevier Sequoia S.A., Lausanne— printed in the Netherlands, presented Apr. 7–11, 1980 at the International Symposium on the Properties and Applications of Metal Hydrides, Colorado Springs, CO USA.

* cited by examiner

Primary Examiner—Helen Kwok
Assistant Examiner—David J. Wiggins

(57) ABSTRACT

An apparatus and method for measuring the quantity of hydrogen in a hydrogen storage vessel of a hydrogen fuel cell using the Pressure, Composition, Temperature (PCT) relationship of the storage media is disclosed. The method of measuring the quantity of hydrogen involves, measuring the temperature 310 of the hydrogen storage media at one or more points on the hydrogen storage vessel 300, measuring the mechanical strain 320 at one or more points on the hydrogen storage vessel, computing the pressure 330 inside the vessel based on the strain measurements, referring to a lookup table 340 or an equation representing the discharge PCT curve for the particular composition of the hydrogen storage media at the measured temperature and computing the hydrogen concentration at the measured pressure. The changes in temperature and pressure during hydrogen absorption-desorption which are characteristic of hydride storage media air is used to measure the hydrogen concentration in the storage vessel and the hydrogen to metal hydride.

24 Claims, 5 Drawing Sheets

METHOD AND APPARATUS FOR DETERMINING THE AMOUNT OF HYDROGEN IN A VESSEL

TECHNICAL FIELD

This invention relates in general to fuel cells, and more particularly to a method and a system for measuring the amount of hydrogen in a hydrogen storage vessel.

BACKGROUND

In recent years, nearly all electronic devices have been reduced in size and made lightweight, in particular portable electronic devices. This advancement has been made possible, in part, by the development of new battery chemistries such as nickel-metal hydride, lithium ion, zinc-air, and lithium polymer, that enable larger amounts of power to be packaged in a smaller container. These secondary or rechargeable batteries need to be recharged upon depletion of their electrical capacity. This is typically performed by connecting the battery to a battery charger that converts alternating current to a low level direct current of 2–12 volts. The charging cycle typically lasts a minimum of 1–2 hours, and more commonly 4–14 hours. Although the new batteries are a tremendous advancement over the previous generations of batteries, they still suffer from the need for sophisticated charging regimens and the slow charging rates.

Fuel cells are expected to be the next major source of energy for portable electronic products. Simply put, fuel cells catalytically convert a hydrogen molecule to hydrogen ions and electrons, and then extract the electrons through a membrane as electrical power, while oxidizing the hydrogen ions to $H_2O$ and extracting the byproduct water. The tremendous advantage of fuel cells is the potential ability to provide significantly larger amounts of power in a small package, as compared to a battery.

Their potential ability to provide long talk-times and standby times in portable communication device applications are driving miniaturization of fuel cell technologies. The Polymer Electrolyte Membrane (PEM) based air-breathing, dead-ended fuel cells are ideally suited for powering portable communication devices. The most mature of the fuel storage technologies for this class of fuel cells is hydride materials packed in a container which stores hydrogen and releases it on demand. Storage of hydrogen in a container containing reversible metal hydride is a common practice in the field of fuel cells.

A fundamental customer requirement for any form of portable power source is the ability to measure and communicate the capacity remaining in the source (how long can it power the device?). In addition, the remaining capacity has to be continually measured while the device is in operation so as to provide the user current status of the power source. In fuel cell systems, as the energy storage and energy conversion aspects are decoupled, the key to measuring remaining capacity depends on the ability to accurately measure the amount of fuel remaining in the storage vessel. In portable devices with fuel cell power sources, the remaining energy capacity is directly dependent on the amount of fuel remaining in the fuel storage vessel. Since many fuel cell applications use hydrogen stored in solid medium such as metal hydrides, chemical hydrides and nano fibers, methods and systems to measure the quantity of hydrogen stored in these media is a necessity for the successful development of these technologies for commercial applications.

Though prior art technologies exist to measure the pressure in a hydride vessel, they do not accurately measure the quantity of hydrogen in the vessel due to the dependence of hydrogen concentration on parameters in addition to the pressure inside the fuel storage vessel. Also, the prior art methods can be used only under equilibrium conditions where the system is not discharging hydrogen to a fuel cell or other load device. Another critical factor to consider is the differences between the charge and discharge characteristics of the storage media. Due to hysteresis, the hydrogen discharge characteristics of the storage medium is different from the charge characteristics. In addition the shortcomings of the prior art techniques described above, they also fail to take into account the degradation of hydrogen storage capacity of the hydride material over time as the percentage of active hydride in the overall composition decreases over time.

DETAILED DESCRIPTION OF THE PREFERRED EMBODIMENT

An apparatus and method for measuring the quantity of hydrogen in a hydrogen storage vessel of a hydrogen fuel cell using the Pressure, Composition, Temperature (PCT) relationship of the storage media is disclosed. The method of measuring the quantity of hydrogen involves measuring the temperature of the hydrogen storage media at one or more points on the hydrogen storage vessel, measuring the mechanical strain at one or more points on the hydrogen storage vessel, computing the pressure inside the vessel based on the strain measurements, referring to a lookup table or an equation representing the discharge PCT curve for the particular composition of the hydrogen storage media at the measured temperature and computing the hydrogen concentration at the measured pressure. The changes in temperature and pressure during hydrogen absorption-desorption which are characteristic of hydrogen storage media composition is used to measure the concentration ratio of hydrogen to hydrogen storage media.

Figure 1:
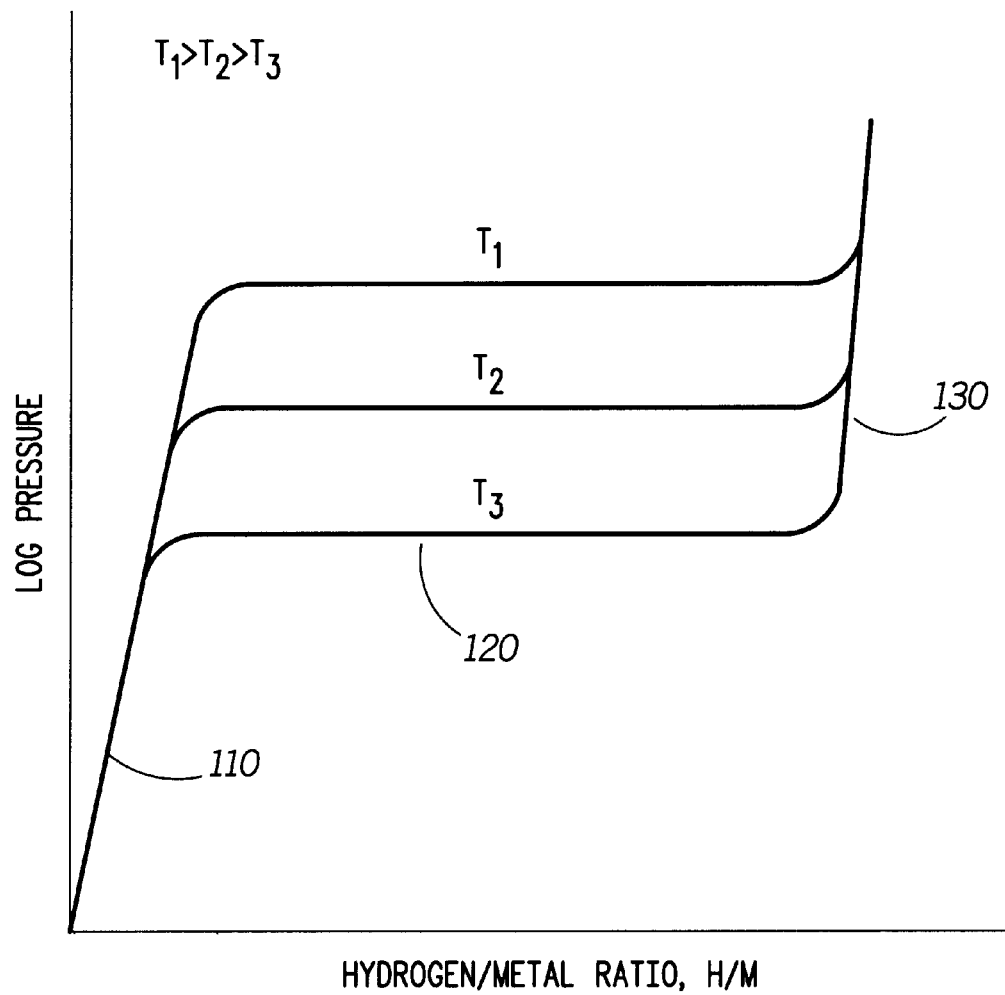
FIG. 1 is a schematic representation of ideal relationship between pressure, composition and temperature during absorption of hydrogen by metal hydrides.

FIG. 1 illustrates the hydrogen absorption and desorption properties of metals as pressure-composition isotherms. In FIG. 1, hydrogen to metal ratio, which is a ratio of the quantity of hydrogen in the hydrogen storage media to the quantity of hydrogen storage media, is shown on the abscissa of the graph and natural logarithm of the pressure inside the hydrogen storage vessel is shown on the Y-axis of the graph. Most elemental metals will absorb hydrogen when gaseous hydrogen ($H_2$) is brought into contact with the metal (M) surface. Some of the metals and alloys of interest for storing hydrogen are: Lanthanum-Nickel, Calcium-Nickel, Magnesium-Nickel, Iron-Nickel, Iron-Tin, Vanadium, Palladium, etc. In this phase, hydrogen exists in solution in the metal. The absorption can be written as: $H_2+M \leftrightarrows MH_2$. The use of the double arrow means that the reaction can occur in both directions. The pressure of the hydrogen gas determines the direction. At high initial pressure, hydrogen goes into the metal. After a period of time, equilibrium is reached and hydrogen goes into the metal at the same rate as it leaves the metal. If the hydrogen gas pressure is reduced, hydrogen will flow out of the metal and into the surrounding environment. If the environment is a closed vessel, the pressure will eventually build up to a point where equilibrium is reached once again. This simple hydrogen absorption process is represented by the linear portion 110 of the absorption curve in FIG. 1.

In a metal hydride system, once above a certain pressure, the hydrogen gas ($H_2$) is absorbed onto the metal surface, where it dissociates into hydrogen atoms (H) and enters interstitial sites in the lattice. In this second phase, hydrogen atoms can be added to the metal without any corresponding increase in pressure. The plateau region 120 in FIG. 1 represents what is called the two-phase equilibrium region. Saturation is reached at a value of the hydrogen to metal ratio (H/M) where all of the interstitial sites have been filled. At that point no more hydrogen can be added to the metal lattice and further increase in hydrogen requires a corresponding increase in pressure as represented by the third region 130. This entire process is reversible with some degree of hysteresis. FIG. 1 shows the ideal absorption-desorption pressure-composition isotherm for a metal-hydrogen system where the plateau pressure is constant. In reality, while such isotherms as shown in FIG. 1 might be achievable, most hydrides deviate from this ideal behavior. In addition to the fact that the plateau region slopes and the boundaries of this region are not as well defined, there also exists hysteresis between absorption and desorption curves.

Figure 2:
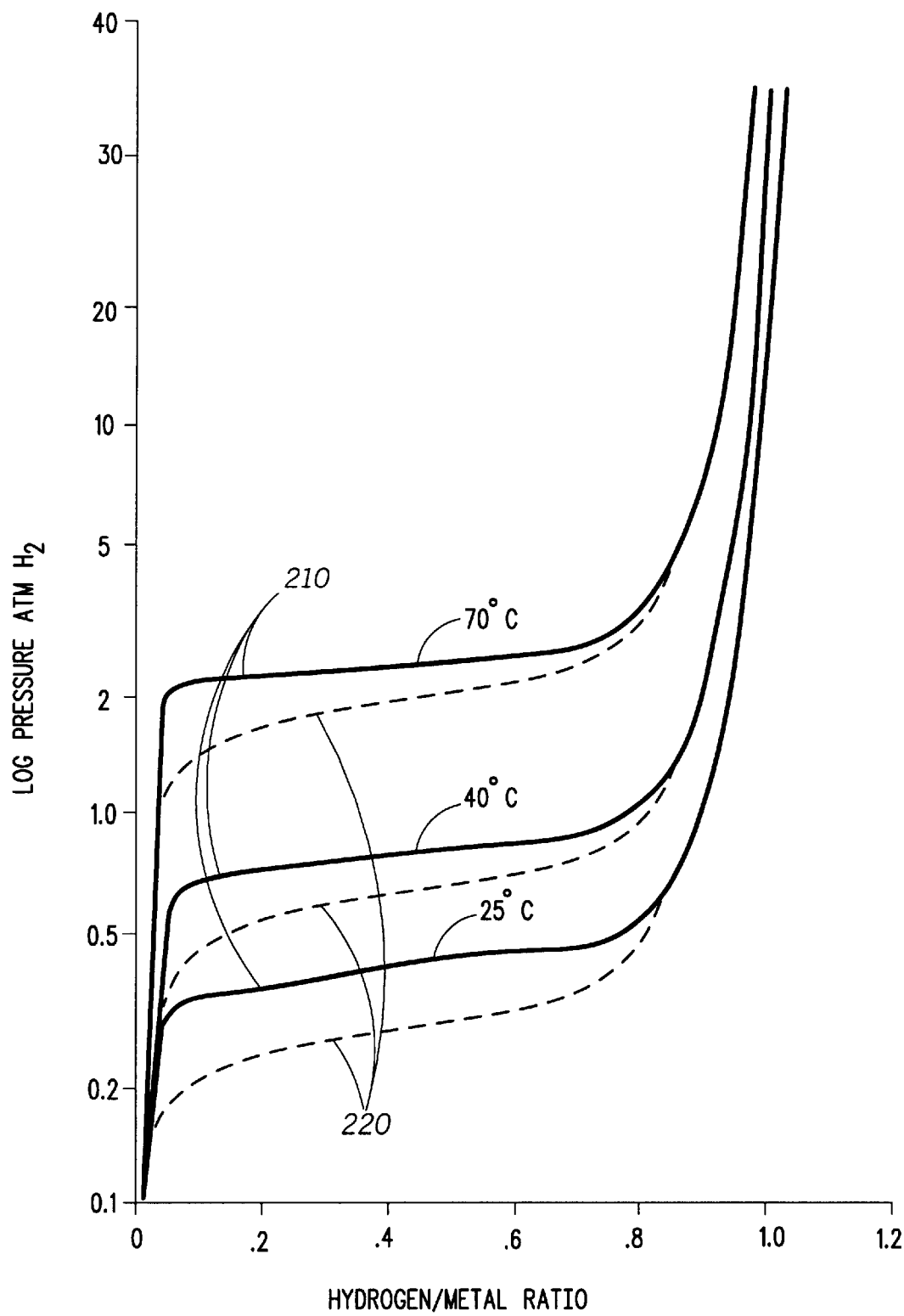
FIG. 2 is a schematic representation of realistic relationship between pressure, composition and temperature during absorption and desorption of hydrogen by a metal hydride.

FIG. 2 schematically shows more realistic versions of the absorption-desorption pressure-composition isotherms including the slope at the plateau region and the hysteresis effect. The absorption isotherms 210 show the relationship between pressure and hydrogen concentration during charging phase while desorption isotherms 220 show the relationship between pressure and hydrogen concentration during discharge phase.

While a fuel cell is operating, it draws hydrogen from the hydrogen storage vessel and this discharge operation typically is designed to operate at the plateau region of the curves shown in FIG. 2. The discharge operation can be nearly isothermal or it can involve temperature changes depending on the rate of discharge and the operating pressure of the fuel cell that is attached to the storage vessel. The nearly isothermal process is an efficient method wherein the stored hydrogen gas is released from the storage media by reducing the hydrogen gas pressure, preferably to a value, which is lower than the plateau pressure at essentially the same temperature. The temperature is kept nearly constant by removing heat during sorption and adding heat during desorption. Another less preferred process is a thermal-swing system wherein the hydrogen is absorbed at low temperature and desorbed at a higher temperature. However, this process has higher heating and cooling requirements. A third mode of operation is a modified isothermal process wherein a moderate thermal swing is permitted to allow hydrogen desorption at relatively higher pressure.

Therefore, for hydrogen storage materials that have a sloped plateau region, based on the interrelation of temperature, pressure and hydrogen content, at any given temperature, the hydrogen content of the material is determined by the partial pressure of the hydrogen in contact with that material. Generally, as temperature rises it takes a greater partial pressure of hydrogen to maintain a given concentration of hydrogen in the material. The converse is also true as temperature decreases.

Figure 3:
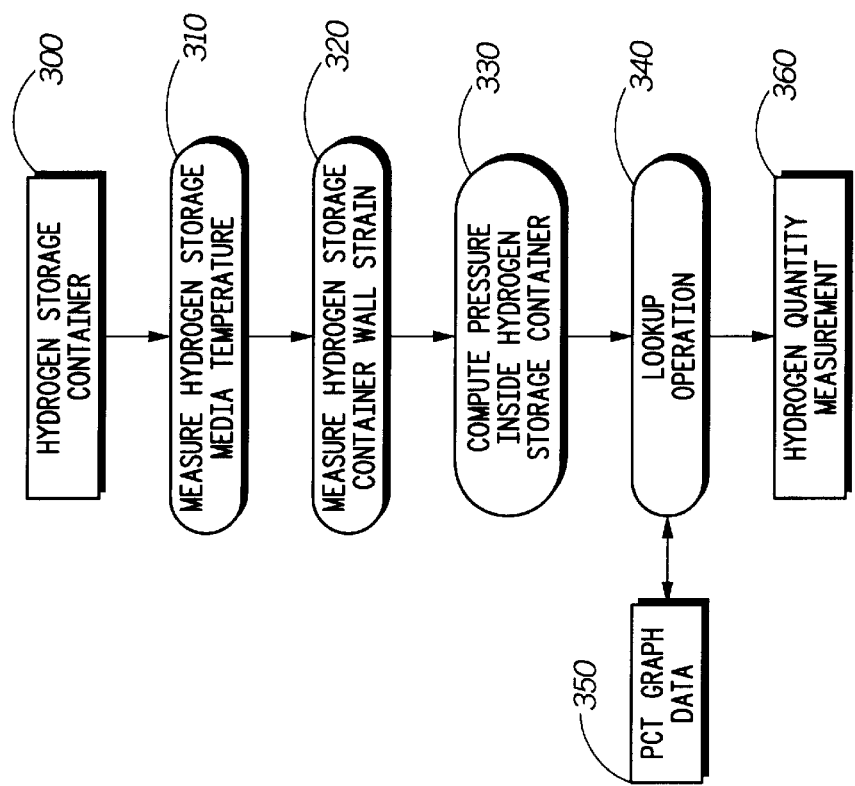
FIG. 3 is a process flow diagram in accordance with a first embodiment of the hydrogen measurement method of the present invention.

A typical flow chart of the process used to measure the quantity of hydrogen in a hydrogen storage vessel according to a first embodiment of the present invention is shown in FIG. 3 where the rectangular boxes represent structural entities in the process, and boxes with rounded corners represent process steps to achieve the various structural entities. Referring now to FIG. 3, the measurement process starts with measuring temperature 310 of a hydrogen storage media inside the hydrogen storage vessel 300. Typical measurement methods that are appropriate for this task are thermocouples, thermistors, resistors, infrared sensors and diodes. At the same time, the pressure inside the storage vessel is measured by measuring strain 320 of the hydride vessel wall. Following the strain measurement step, the pressure inside the storage vessel is computed 330 based on the geometry and material property of the vessel and the strain gage calibration. Once the pressure and temperature are known at a point in time, the lookup operation 340 is performed which selects the hydrogen concentration corresponding to the measured pressure on an isotherm 340 corresponding to the measured temperature from a PCT graph 350 for the particular hydride composition used in the hydrogen storage vessel 300. The isotherm 340 used in the lookup step is one of the desorption isotherms 220 corresponding to a particular temperature. If an isotherm does not exist for a measured temperature, it is generated by interpolation and extrapolation as necessary from the isotherms that are at temperatures immediately above and below the measured value.

Although the preferred embodiment has listed some of the more commonly used temperature and pressure measurement methods, the present invention is not necessarily limited by the use of these methods. Any temperature and pressure measuring method well known in the art can be used within the structure described in the preferred embodiment.

Figure 4:
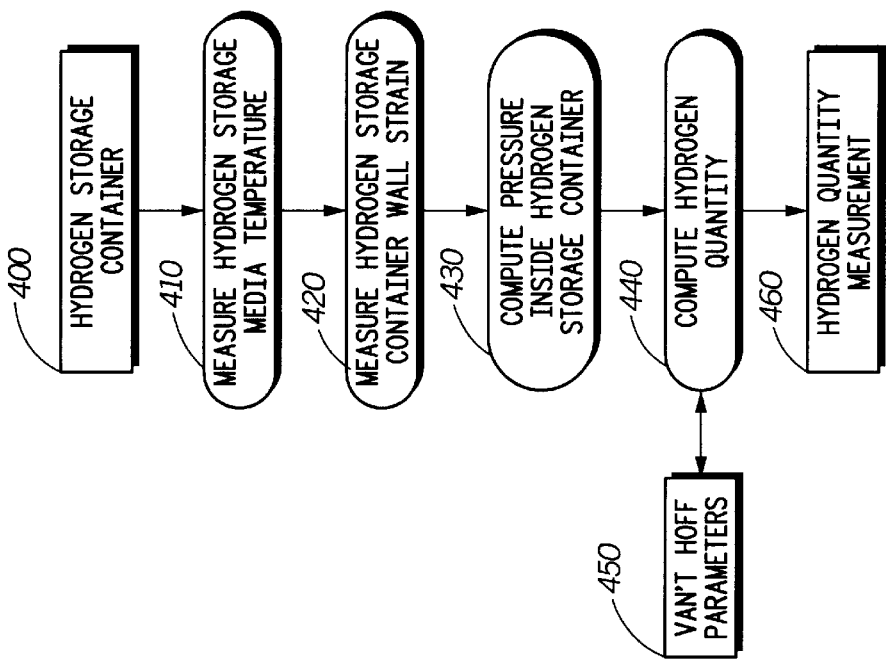
FIG. 4 is a process flow diagram in accordance with a second embodiment of the hydrogen measurement method of the present invention.

An alternate embodiment of the present invention is shown in FIG. 4. This embodiment uses van't Hoff relationship $$x = \frac{2\Delta H}{RT}\left(\frac{1}{\ln P - C}\right)$$

which is a mathematical relationship between partial pressure, composition and temperature for hydrogen storage materials to compute the quantity of hydrogen in the vessel. In the above relationship x is the quantity of hydrogen in the vessel, P is the measured pressure inside the vessel, T is the temperature of the storage medium, R is the universal gas constant, $\Delta H$ is the change in enthalpy which is a function of the temperature T and C is a constant for a given composition of the hydride material. In this figure, the lookup operation 340 is replaced by the a computational operation 440. The computational operation uses stored van't Hoff parameters 450 to compute the quantity of hydrogen.

Figure 5:
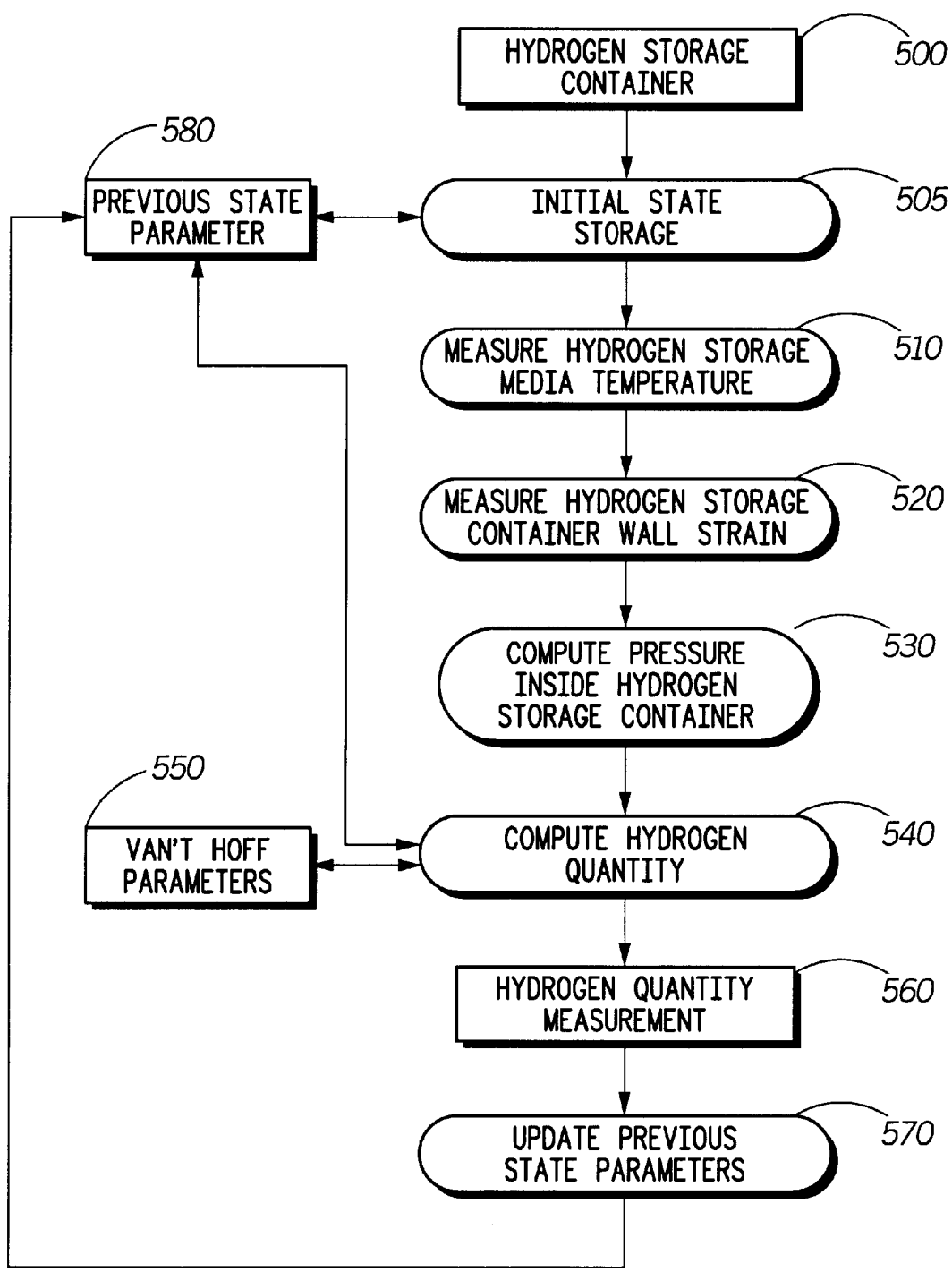
FIG. 5 is a process flow diagram in accordance with a third embodiment of the hydrogen measurement method of the present invention.

Yet another embodiment of the present invention is shown in FIG. 5. This embodiment uses the change in temperature and pressure between a known initial state and the current condition to compute the quantity of hydrogen remaining in the storage vessel using a differential version of the van't Hoff relationship $$\Delta x = \left[\frac{2\Delta H}{R}\right]\left[\frac{\Delta \frac{1}{T}}{\Delta \ln P}\right]$$

which a is mathematical relationship between change in partial pressure, composition and change in temperature for hydrogen storage materials. In the above relationship $\Delta x$ is the net change in quantity of hydrogen in the vessel, $\Delta \ln P$ is the change in measured pressure inside the vessel, $\Delta(\frac{1}{T})$ is the change in temperature of the storage medium, R is the universal gas constant and $\Delta H$ is the change in enthalpy which is a function of the temperature T and the hydride composition. In this embodiment, the pressure and temperature measurements are taken at the beginning when the quantity of hydrogen stored in the hydrogen storage vessel is known. This value of temperature, pressure and quantity of hydrogen is stored in the state storage means 580 for future use. This initialization step 505 can be performed at the end of charging the hydrogen storage vessel. During device operation when hydrogen is being discharged, the measurement process starts with measuring temperature 510 of a hydrogen storage media inside the hydrogen storage vessel 500. Typical measurement methods that are appropriate for this task are thermocouples, thermistors, resistors, RTD, infrared sensors and diodes. At the same time, the pressure inside the storage vessel is measured by measuring strain 520 of the hydride vessel wall. Following the strain measurement step, the pressure inside the storage vessel is computed 530 based on the geometry and material property of the vessel and the strain gage calibration. Once the pressure and temperature are known at a point in time, a computational operation 540 is performed. The computational operation uses stored van't Hoff parameters 550, the stored previous state parameters 580 and the differential form of the van't Hoff relationship shown above. The computational step estimates the remaining quantity of hydrogen by subtracting the change in quantity of hydrogen from the initial quantity. After the computation is complete, the previous state parameters 580 are updated 570 with current state parameters, temperature, pressure, and quantity of remaining hydrogen. These will serve as previous state parameters for the next measurement cycle. Since only the change in temperature and pressure are used for estimating the quantity of hydrogen using this method, the hydride composition dependent terms are eliminated from the van't Hoff's relation. Therefore his embodiment is well suited for measuring the quantity of remaining hydrogen in a vessel using hydride materials that degrade significantly over time due to many charge/discharge cycles.

Figure 6:
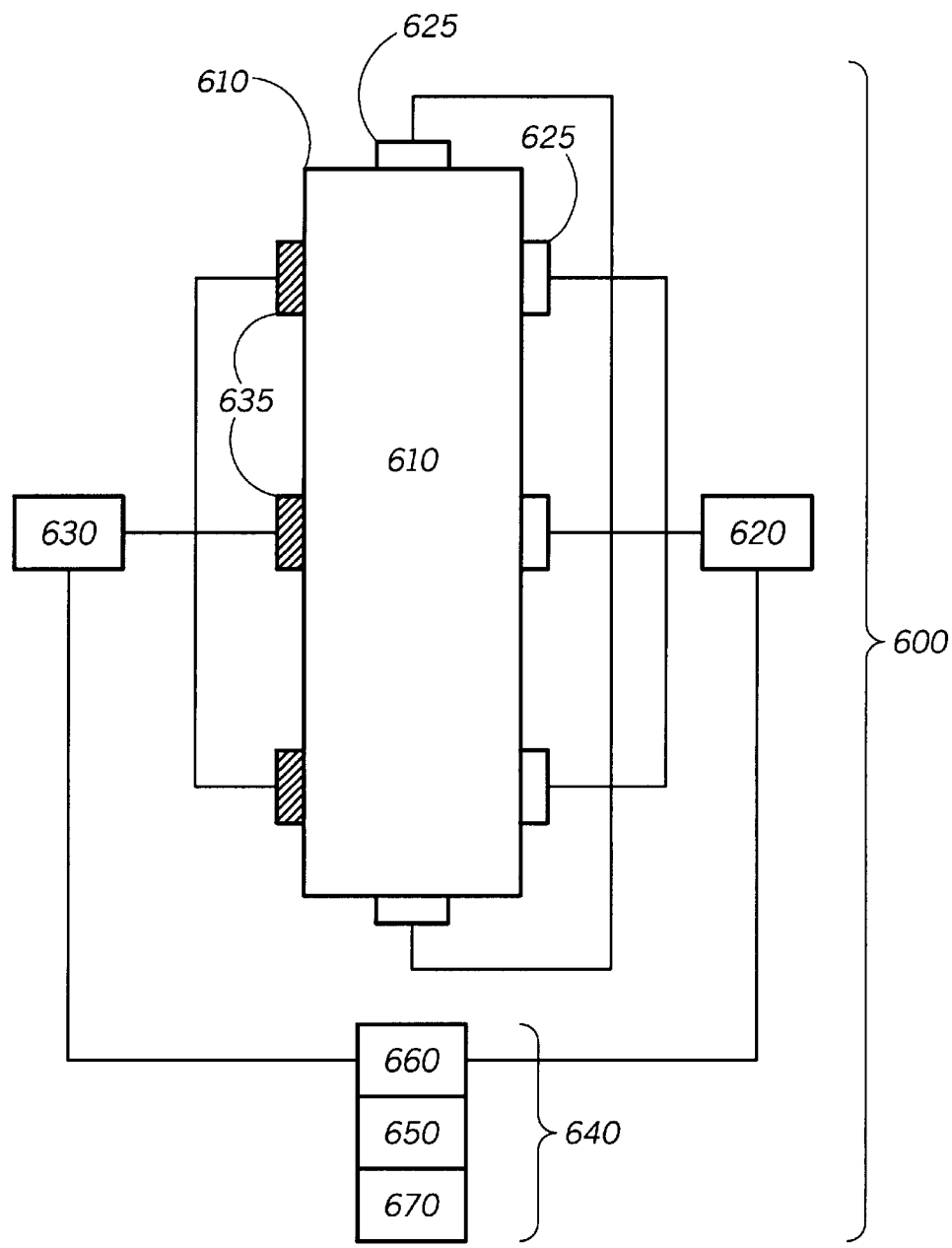
FIG. 6 is a schematic representation of an apparatus to implement the hydrogen measurement method in accordance with the present invention.

An apparatus to implement the hydrogen measurement method described in the first embodiment of the present invention consists of a storage vessel having hydrogen absorbing material such as metal hydrides, temperature and strain measurement systems and an estimating element that performs the computations, storage and lookup necessary to estimate the quantity of hydrogen in the vessel from the temperature and pressure measurements. FIG. 6 shows a schematic view of an apparatus for implementing the method to measure the quantity of hydrogen in a vessel with hydrogen storage media. The apparatus 600 consists of a hydrogen storage vessel 610, a temperature measurement means 620, a strain measurement means 630 and an estimating element 640 that performs the computations, storage and lookup functions. The temperature measurement means 620 consists of one or more temperature probes 625 distributed on the storage vessel 600 and interconnected with each other. In the preferred embodiment, the temperature of the hydride vessel is measured using resistance thermometry which is based on using a material whose resistivity changes as a function of temperature. The standard commercial resistance sensors utilize nickel or nickel/manganin grids, although special-purpose gages are also available in copper foil grids. These temperature sensors are bonded to structures using standard strain gage installation techniques, and can measure surface temperatures from −269 to +260° C. Because of their extremely low thermal mass and the large bonded area, the sensors follow temperature changes in the structural mounting surface with negligible time lag. Some of the models of resistance temperature sensors made by Measurements Group Inc. of Raleigh, N.C., which are appropriate for this invention are: ETG-50A 50 ohms; Special Purpose, ETG-50B 50 ohms; Special Purpose, WTG-50A 50 ohms; Special Purpose, WTG-50B 50 ohms; Special Purpose, WWT-TG-W200B-050 50 ohms. The temperature probes are connected to the estimating element 640 to provide temperature measurement on demand.

In addition to providing temperature data, the output from the resistance temperature sensors are also used to provide temperature compensation of the strain gage measurement. Since the typical vessels used for storage of hydrogen in hydrogen cell applications are metals that have good thermal conductivity, the temperature of the media can be indirectly measured with reasonable accuracy by measuring the temperature at one or more points on the outside of the hydrogen storage vessel.

The pressure inside the hydride vessel can be reliably measured by measuring the strain on the outside of the hydride vessel. The strain measurement means 630 consists of one or more strain gages distributed on the storage vessel 610 and interconnected with each other. Many different techniques can be used to measure the strain. In the preferred embodiment, a standard strain gage or a strain gage rosette is used to measure the strain. Some of the models of strain gages made by Entran Devices, Inc. of Fairfield, N.J. which are appropriate for this application are: ENTRAN® "bar" and "U" shaped strain gage configurations that are delivered in the following models: ESB-020-350, ESB-020-500 and ESU-025-500. The temperature calibration and compensation of the strain gage is implemented using the measured valued of temperature from the measurement means 630.

The estimating element 640 has a computing component 650, a measurement interface 660, and a storage element 670. The computing component performs the computations and lookup necessary to convert the measured strain values to pressure, interpolation between the isotherms and estimate the quantity of hydrogen remaining in the vessel. The measurement interface 660 activates the strain gages and the temperature probes as needed, provides necessary temperature compensation of strain gage, combines output from multiple probes and gages and communicates the consolidated values to the computing component. The storage element stores the composition of the hydride material, the absorption-desorption PCT isotherms for the particular hydride, geometry and parameter information about the vessel as well as calibration parameters for the other elements.

Although the all the embodiments of the invention have referred to hydride materials as the hydrogen storage media, any other hydrogen storage material well known in the art that exhibits unique PCT relationship can be used within the structure described in the different embodiments.

The present invention enables accurate measurement of quantity of hydrogen in a vessel with hydrogen storage media. This ability to measure quantity of hydrogen will lead to the realization of the hydrogen cell systems which can provide accurate estimates of the energy capacity available in the system during their operation. It achieves these results by using the unique absorption-desorption PCT relationship of different hydrogen storage media which are used to store the fuel used by the fuel cell. This method of using inherent uniqueness in the properties of hydrogen storage materials eliminates the problems encountered with the prior art schemes. Thus, the present invention provides a method and an apparatus for measuring the quantity of hydrogen in a hydrogen storage vessel which overcomes the disadvantages of the prior-art methods and devices of this general type. This novel measurement method is simple to implement and control. The present invention advances the art of accurately measuring the quantity of hydrogen in a hydrogen storage system under dynamic discharge conditions. It has the additional advantage of being able to account for degradation in storage capacity of the media.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims.

What is claimed is:

1. A method for determining the amount of hydrogen in a hydrogen storage vessel containing a known quantity of hydrogen storage media, comprising:

measuring temperature at one or more points on the hydrogen storage vessel and calculating an average temperature for the hydrogen storage media;

measuring mechanical strain at one or more points on the hydrogen storage vessel and computing the pressure inside the hydrogen storage vessel based on the measured mechanical strain;

selecting a pressure, composition, temperature (PCT) operating curve from a family of PCT curves for the hydrogen storage media, based on the calculated average temperature;

selecting an operating point on the selected PCT operating curve, corresponding to the computed pressure inside the hydrogen storage vessel;

determining a value of hydrogen to metal ratio on the selected PCT operating curve corresponding to the selected operating point; and computing the quantity of hydrogen in the hydrogen storage vessel by multiplying the looked up hydrogen to metal ratio value by the quantity of hydrogen storage media.

2. The method of claim 1, wherein the PCT curve used is an absorption curve associated with the charging characteristics of the hydrogen storage media.

3. The method of claim 1, wherein the PCT curve used is a desorption curve associated with the discharge characteristics of the hydrogen storage media.

4. The method of claim 1, wherein the PCT curve is stored as ordinate and abscissa parameter values in a lookup table.

5. The method of claim 1, wherein the PCT curve is defined by the van't Hoff relation $$x = \frac{2\Delta H}{RT}\left(\frac{1}{\ln P - C}\right)$$

wherein x is the quantity of hydrogen in the hydrogen storage vessel, P is the computed pressure inside the hydrogen storage vessel, T is the calculated average temperature of the hydrogen storage media, R is the universal gas constant which has a value of 8.314 kiloJoule/kilomole Kelvin, $\Delta H$ is the change in enthalpy of the hydrogen storage media and C is an empirically determined constant for the hydrogen storage media.

6. The method of claim 1, wherein the hydrogen storage media is selected from the group consisting of metal hydrides, chemical hydrides, organic hydrides and single walled carbon nanotubes.

7. A method for determining the amount of hydrogen in a hydrogen storage vessel containing a known quantity of hydrogen storage media, while the hydrogen storage vessel is discharging hydrogen, comprising:

measuring temperature at one or more points on the hydrogen storage vessel and calculating an average temperature for the hydrogen storage media;

measuring mechanical strain at one or more points on the hydrogen storage vessel and computing the pressure inside the hydrogen storage vessel based on the measured mechanical strain;

selecting a pressure, composition, temperature (PCT) operating curve from a family of PCT curves for the hydrogen storage media, based on the calculated average temperature;

selecting an operating point on the selected PCT operating curve, corresponding to the computed pressure inside the hydrogen storage vessel;

determining a value of hydrogen to metal ratio on the selected PCT operating curve corresponding to the selected operating point; and computing the quantity of hydrogen in the hydrogen storage vessel by multiplying the looked up hydrogen to metal ratio value by the quantity of hydrogen storage media.

8. The method of claim 7, wherein the PCT curve used is the desorption curve associated with the discharge characteristics of the hydrogen storage media.

9. The method of claim 7, wherein the PCT curve is stored as ordinate and abscissa parameter values in a lookup table.

10. The method of claim 7, wherein the PCT curve is defined by the van't Hoff relation $$x = \frac{2\Delta H}{RT}\left(\frac{1}{\ln P - C}\right)$$

wherein x is the quantity of hydrogen in the hydrogen storage vessel, P is the computed pressure inside the hydrogen storage vessel, T is the calculated average temperature of the hydrogen storage media, R is the universal gas constant which has a value of 8.314 kiloJoule/kilomole Kelvin, $\Delta H$ is the change in enthalpy of the hydrogen storage media and C is an empirically determined constant for the hydrogen storage media.

11. The method of claim 7, wherein the hydrogen storage media is selected from the group consisting of metal hydrides, chemical hydrides, organic hydrides and single walled carbon nanotubes.

12. A method for determining change in quantity of hydrogen in a hydrogen storage vessel containing a known quantity of hydrogen storage media in a known initial state, comprising:

storing initial state parameters, comprising quantity of hydrogen in the hydrogen storage vessel, temperature of the hydrogen storage media at the initial state and pressure inside the hydrogen storage vessel at the initial state;

measuring temperature at one or more points on the hydrogen storage vessel and calculating an average temperature for the hydrogen storage media;

measuring mechanical strain at one or more points on the hydrogen storage vessel and computing the pressure inside the hydrogen storage vessel based on the measured mechanical strain;

selecting van't Hoff parameters by referring to a lookup table for the hydrogen storage media; and computing the change in quantity of hydrogen using a differential form of van't Hoff relation $$\Delta x = \left[\frac{2\Delta H}{R}\right]\left[\frac{\Delta \frac{1}{T}}{\Delta \ln P}\right]$$

wherein $\Delta x$ is the change in quantity of hydrogen in the hydrogen storage vessel, $\Delta \ln P$ is the difference between the pressure inside the hydrogen storage vessel at the initial state and the computed pressure inside the hydrogen storage vessel, $\Delta \frac{1}{T}$ is the difference between reciprocal of the temperature of the hydrogen storage media at the initial state and the reciprocal of the calculated average temperature of the hydrogen storage media, R is the universal gas constant which has a value of 8.314 kiloJoule/kilomole Kelvin, and $\Delta H$ is the change in enthalpy of the hydrogen storage media; and updating the stored initial state parameters with the calculate average temperature, the computed pressure and the computed change in quantity of hydrogen.

13. The method of claim 12, wherein the step of measuring pressure further comprises measuring mechanical strain at one or more points on the hydrogen storage vessel and computing the pressure inside the vessel based on the strain measurements.

14. The method of claim 12, wherein the PCT curve used is the absorption curve associated with the charging characteristics of the hydrogen storage media.

15. The method of claim 12, wherein the PCT curve used is the desorption curve associated with the discharge characteristics of the hydrogen storage media.

16. The method of claim 12, wherein the hydrogen storage media is selected from the group consisting of metal hydrides, chemical hydrides, organic hydrides and single walled carbon nanotubes.

17. A system to determine the quantity of hydrogen in a hydrogen storage vessel containing a known quantity of hydrogen storage media, comprising:

a means for measuring pressure inside the hydrogen storage vessel;

a means for measuring temperature at one or more points on the vessel and calculating an average of the measured temperatures; and a computational means for estimating the quantity of hydrogen in the hydrogen storage vessel; wherein the computational means selects a pressure, composition, temperature (PCT) operating curve from a family of PCT curves for the hydrogen storage media, based on the calculated average temperature;

selects an operating point on the selected PCT operating curve, corresponding to the measured pressure inside the hydrogen storage vessel;

determining a value of hydrogen to metal ratio on the selected PCT operating curve corresponding to the selected operating point; and computes the quantity of hydrogen in the hydrogen storage vessel by multiplying the looked up hydrogen to metal ratio value by the quantity of hydrogen storage media.

18. The system of claim 17, wherein the PCT curve used is the absorption curve associated with the charging characteristics of the hydrogen storage media.

19. The system of claim 17, wherein the PCT curve used is the desorption curve associated with the discharge characteristics of the hydrogen storage media.

20. The system of claim 17, wherein the PCT curve is stored as ordinate and abscissa parameter values in a lookup table.

21. The system of claim 17, wherein the PCT curve is defined by the van't Hoff relation $$x = \frac{2\Delta H}{RT}\left(\frac{1}{\ln P - C}\right)$$

wherein x is the quantity of hydrogen in the hydrogen storage vessel, P is the measured pressure inside the hydrogen storage vessel, T is the calculated average temperature of the hydrogen storage media, R is the universal gas constant which has a value of 8.314 kiloJoule/kilomole Kelvin, $\Delta H$ is the change in enthalpy of the hydrogen storage media and C is an empirically determined constant for the hydrogen storage media.

22. The system of claim 17, wherein the hydrogen storage media is selected from the group consisting of metal hydrides, chemical hydrides, organic hydrides and single walled carbon nanotubes.

23. The system of claim 17, wherein the means for measuring temperature is selected from the group consisting of thermocouples, thermistors, resistors, infrared sensors and diodes.

24. The system of claim 17, wherein the means for measuring pressure is selected from the group consisting of strain gages, manometers and pressure gages.

* * * * *